United States Patent [19]

Paton

[11] 4,413,760

[45] Nov. 8, 1983

[54] DISPENSING DEVICE HAVING RATCHET MEMBER

[75] Inventor: John S. Paton, Beith, Scotland

[73] Assignee: Greater Glasgow Health Board, Glasgow, Scotland

[21] Appl. No.: 249,448

[22] Filed: Mar. 31, 1981

[30] Foreign Application Priority Data

Apr. 8, 1980 [GB] United Kingdom ............... 8011572

[51] Int. Cl.³ .............................................. B67D 5/42
[52] U.S. Cl. ..................................... 222/309; 222/43; 222/391
[58] Field of Search ..................... 206/537; 222/41, 43, 222/129, 130, 131, 173, 183, 309, 325, 326, 327, 328; 221/283

[56] References Cited

U.S. PATENT DOCUMENTS

| 1,997,129 | 4/1935 | Taylor et al. | 222/309 |
| 2,605,763 | 8/1952 | Smoot | 222/43 |
| 2,718,299 | 9/1955 | Atwater et al. | 206/537 |
| 3,348,545 | 10/1967 | Sarnoff et al. | 222/237 |
| 3,613,952 | 10/1971 | Gilmont | 222/43 |

Primary Examiner—Joseph J. Rolla
Assistant Examiner—Jan Koniarek
Attorney, Agent, or Firm—Murray & Whisenhunt

[57] ABSTRACT

This invention relates to a dispensing device (1) suitable for use in dispensing a predetermined quantity of material from a container comprising a tubular body member (2) having an outlet (6) at one end, and a plunger (17) slidably movable in said body member. The dispensing device comprises an elongate body (3), and a first drive member (10) mounted in the body (3) for use in driving said plunger (17).

According to the invention the first drive member (10) is mounted for driving engagement via an unidirectional drive transmission (12,13), with a second drive member (14) having a free end (15,16) drivingly engagable with the plunger (17) of the container, so that said second drive member (14) and the plunger (17) can be driven by the first drive member (10) via the unidirectional drive transmission members (12,13), only in a direction towards the container outlet (6) while permitting return movement of the first drive member (10).

8 Claims, 3 Drawing Figures

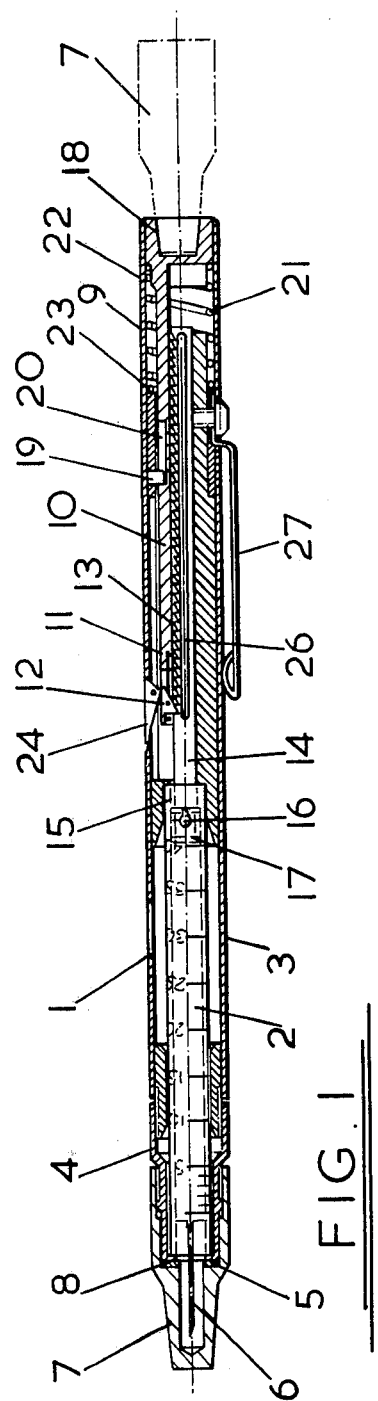
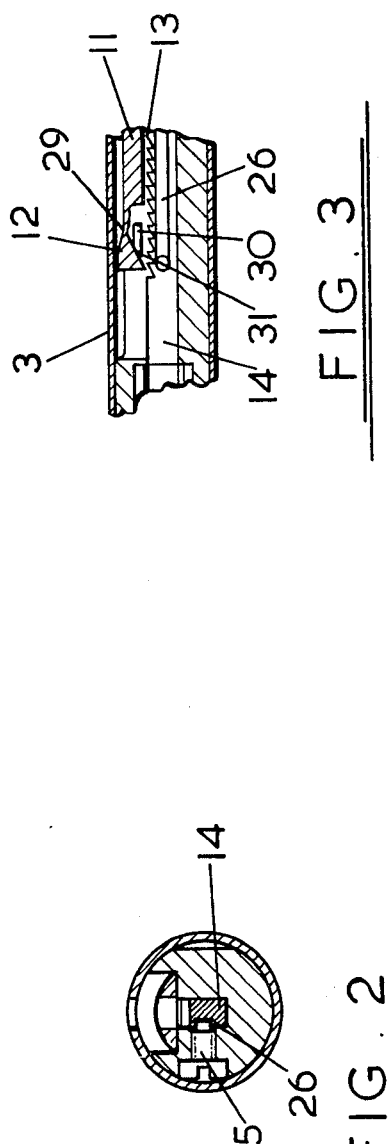

DISPENSING DEVICE HAVING RATCHET MEMBER

The present invention relates to a device suitable for use in dispensing material from a container, such as a hypodermic syringe and in particular to a dispensing device suitable for use in dispensing a predetermined quantity of material from a container comprising a tubular body member having an outlet at one end, and a plunger slidably movable in said body member towards said outlet, said dispensing device comprising an elongate body having a chamber for receiving a said container with said outlet held in a first end portion of the elongate body, and a first drive member mounted in said body for use in driving said plunger.

It has previously been proposed to provide conventional hypodermic syringes with adjustable stop means on either the tubular body or the piston rod to facilitate dispensing. Apart from indicating the end point of dispensing though, this does not avoid the need for the routine steps and precautions of expelling all air from the container prior to injection, or permit successive dispensing of a plurality of doses without the need for carefully checking and controlling the starting point on each occasion insofar as the plunger is not prevented from return movement.

A different approach is incorporated in the so-called Palmer injector. In this the device in use is generally in the form of a handgun with a lever operated in the manner of a trigger being employed to release a spring which advances the syringe and needle rapidly and accurately into the skin. Thereafter the syringe is operated in entirely conventional manner. Such a device is however relatively cumbersome and is unsuitable for carrying about in a pocket as would be desirable for, for example a diabetic requiring regular injections of specific doses of insulin.

It is an object of the present invention to provide a dispensing device avoiding or minimising one or more of the above disadvantages.

The present invention provides a dispensing device suitable for use in dispensing a predetermined quantity of material from a container comprising a tubular body member having an outlet at one end, and a plunger slidably movable in said body member towards said outlet, said dispensing device comprising an elongate body having a chamber for receiving a said container with said outlet held in a first end portion of the elongate body, and a first drive member mounted in said body for use in driving said plunger, characterized in that said first drive member is slidably mounted for driving engagement via an unidirectional drive transmission, at least in use of the device, with a second drive member having a free end drivingly engageable with said plunger of the container, in use of the device, so that said second drive member and said plunger can be driven by the first drive member via said unidirectional drive transmission means in use of the device, only in a direction towards the container outlet and the first end portion of the elongate body whilst permitting return movement of the first drive member.

Preferably the unidirectional drive transmission means comprises a ratchet means, the expression "ratchet means" or "mechanism" being used herein to indicate a mechanism in which a pawl mounted on one member is disposed so as to permit relative movement of a ratchet-toothed member having a plurality of ratchet teeth, preferably in a substantially rectilinear arrangement, and mounted on a second member, in a forward direction whilst engaging the ratchet teeth to prevent relative movement in a return direction.

In a further aspect there is provided a dispenser of the invention which includes a said container, which preferably is a hypodermic syringe, most preferably one containing an injectable medicament. In another aspect the invention provides a method of injecting a medicament into the body of a mammal or other animal comprising the steps of puncturing the skin of the mammal or other animal with the needle of a hypodermic syringe mounted in a dispenser of the invention and advancing the first drive member of said dispenser.

With a device of the invention positive and accurate dispensing of material from a suitable container can be achieved by a simple recti-linear movement of a said first drive member which can be simply effected by for example pushing an end thereof, whilst providing protection against the possibility of embolisms resulting from inadvertent injection of air into the body following accidental retraction of the plunger since the drive transmission prevents unintentional retraction of the plunger by the first drive member. At the same time a substantially 'clean' external configuration of the device may be retained thus making it suitable for carrying about on one's person e.g. in a pocket or a handbag without risk of unintentional dispensing or damage to the device.

Further preferred features and advantages of the invention will appear from the following description given by way of example of some preferred embodiments of a dispenser of the invention illustrated with reference to the accompanying drawings in which:

FIG. 1 is a longitudinal section of the dispenser;
FIG. 2 is a transverse section of the dispenser of FIG. 1; and
FIG. 3 is a detail view corresponding to FIG. 1 of a modified embodiment.

FIG. 1 shows a dispensing device 1 in use with a container in the form of a disposable hypodermic syringe 2. The assembly is generally pen-shaped, the dispensing device 1 comprising a barrel in the form of an elongate body member 3 with a screw-threadedly attached detachable front portion 4 which has an opening 5 at its free end through which the needle 6 comprising the outlet of the hypodermic syringe 2 projects. The needle 6 is normally protected by a cap 7 which may be a snap-fit on or screw threadedly engageable with the front body portion 4. A resiliently deformable washer 8 is conveniently provided inside the cap 7 for sealing to the free end of the front body portion 4 thereby to seal the space inside the cap 7 around the needle 6.

In the rear end 9 of the barrel 3 is slidably mounted a first drive member 10 which is provided with, at its forward end 11, a pivotally mounted pawl 12 disposed in engagement with one of a series of ratchet teeth 13 extending along one side of a second slidably mounted drive member 14. It will of course be appreciated that if desired the ratchet teeth 13 could be provided on the first drive member whilst the pawl is provided on the second drive member. The free forward end 15 of the second drive member is formed with a small knob 16 which is resiliently held captive in the resiliently deformable plunger 17 of the hypodermic syringe 2. Although in the present case it is intended that the dispenser be used with a disposable syringe having only a plunger 17, the second drive member could also be part of the disposable syringe being formed, if desired, integrally with the plunger 17—in other words a fresh second drive member is provided each time a new container is inserted.

In the normal position of the device 1, the rear end of the first drive member 10 is disposed so as not to project beyond the rear end 9 of the barrel 3 in order to avoid unintentional dispensing resulting from accidental striking of said drive member 10. The rear end 9 is however provided with a recess 18 in which can locate one end of the cap 7 as shown in chain line. By pushing on the cap 7 e.g. with a thumb, the first drive member 10 may be advanced inside the barrel 3. The pawl 12 at the front end of said first drive member 10 engaged with a ratchet tooth 13 of the second drive member 14 advances the latter correspondingly until the first drive member's progress is halted by a stop member 19 which projects radially inwardly from the barrel 3 to be slidably located in a groove 20 of predetermined length in a side of first drive member 10.

The plunger 17 of the hypodermic syringe is correspondingly advanced by a distance determined by said stop member 19, dispensing a predetermined quantity of liquid or liquid suspension via the needle 6.

When the driving force is withdrawn from the cap 7 the first drive member 10 is returned to its normal position by a resilient biasing means in the form of a helical spring 21 disposed around the rear end of the first drive member 10 for acting between opposed shoulders 22,23 provided on the first drive member 10 and interior wall of the barrel 3. The pawl 12 is, however, able to slip over the ratchet teeth 13 by pivoting to a disengaged position, so that the second drive member 14 and plunger 17 remain in the position to which they have previously been advanced. Repetition of the complete cycle will result in dispensing of a further predetermined quantity of material from the syringe 2.

By making a given number e.g. 5 of the ratchet teeth 13 correspond to the predetermined first drive member maximum displacement as determined by the co-acting groove 20 and stop 19 various predetermined amounts of material may be dispensed in the following manner. The first drive member is advanced as far as possible and then allowed to return gradually under the influence of the spring 21. As it does so the pawl slips over the ratchet teeth 13 one by one making a small click each time. If return is halted after say 2 clicks, and advance of the first drive member resumed as far as it will go, then two fifths of the normal quantity will be dispensed from the syringe 2. From this it will be appreciated that various predetermined quantities of material may be readily dispensed substantially automatically without the need for the user to visually monitor or check the syringe in any way thus enabling the dispenser to be safely used even by a blind person. Most conveniently the device is formed and dimensioned so that when used with a syringe of a predetermined dimensions containing a given solution, the predetermined maximum displacement of the first drive member corresponds to a standard dose of say 5 or 10 units of the material being dispensed whilst each ratchet tooth corresponds to a predetermined fraction e.g. 1/5th of this dose.

In order to enable replacement of the syringe 2, a pivotally mounted lever 24 is mounted in the side of the barrel 3 adjacent the pawl 12 so as to be normally flush with the barrel and extend along the length thereof but be pivotable e.g. with the aid of a finger nail engaged behind a longer end thereof, into a release position in which the shorter end of the lever engages with the holds the pawl 12 in a position out of engagement with the ratchet teeth 13 to enable the second drive member 14 to freely move in either direction independently of the first drive member 10. This enables the second drive member 14 to be fully retracted to a starting position thereof as determined by a guide and stop means in the form of a stop screw 25 (see FIG. 2) which locates in a groove 26 in one side of the second drive member 14. The lever 24 may then be returned to its normal position allowing the pawl 12 to re-engage the ratchet teeth 13. A fully loaded syringe 2 is then inserted into the barrel 3 from the front end thereof (after first removing the front portion 4 and any previously used syringe) until the plunger 17 abuts with or engages the front end 15 of the second drive member 14. The front barrel portion 4 is then replaced and as it is brought into its fully secured position it pushes back the body of the syringe 2 into its starting position, expelling a small amount of liquid and/or any air that might be present in the syringe. This step may be carried out in accordance with conventional syringe handling techniques. If all the air present in the syringe is not expelled at this stage then the expulsion may be completed with the aid of one or more strokes of the dispenser.

In a slightly different alternative procedure e.g. where, as in the drawing, the front end of the second drive member 14 is formed to be resiliently engaged in the syringe plunger 17, this engagement is conveniently effected whilst the second drive member 14 is in a substantially fully extended position and the second drive member 14 only then returned to its starting position, allowing the syringe 2 to follow it into the interior of the barrel 3.

Finally in order to facilitate carrying of the dispenser 1 in a jacket pocket, in the manner of a pen or the like, the barrel 3 is provided with a clip 27 towards its rear end.

Although the above described dispenser is particularly suitable for use with syringes it will be appreciated that other forms of container including a dispensing plunger may also be used especially where dispensing of a predetermined quantity of material is required. Thus, for example there may be used an elongate container having a nozzle with a greater or smaller diameter nozzle and containing a topical medicament such as a lotion or eye drops or indeed any other fluid or material capable of being readily extruded from such a container.

EXAMPLE

A dispenser according to the drawings is dimensioned for holding a 1 ml. capacity syringe which has an internal cross-sectional area of 17.35 $mm^2$ and contains an aqueous insulin suspension containing 80 units of insulin $ml^{-1}$. The groove 20 is dimensioned to provide a maximum stroke length of 7.2 mm corresponding to the advance of 5 ratchet teeth i.e. each ratchet tooth corresponds to an advance of 1.44 mm. Upon insertion of the syringe needle into the arm or leg of a patient and carrying out a single stroke of the first drive member via the cap 10 units of insulin were injected into the patient.

It will be noted from the drawing that the syringe 2 shown therein has an integrally mounted needle. Whilst a syringe with a standard Luer nozzle fitting and a separate needle unit mounted thereon could be employed, this would be rather more cumbersome and necessitate a somewhat more cumbersome barrel construction to accommodate the needle fitting and is therefore less preferred. As a further alternative the syringe 2 could be in the form of a body with a plunger at or towards its rear end and an opening at its forward end sealed by a plug or membrane of a material such as rubber or a similar resiliently deformable polymeric material through which the rear needle of a double ended hypodermic needle unit can be inserted prior to use of the syringe 2.

It will also be noted from the drawing that the syringe 2 omits the finger grip lugs at the rear end of the body as these are not required and may again involve a more complex barrel construction if they were to be retained.

Also as has already been mentioned above the second drive member may itself be part of the disposable syringe. This enables the use of different sized ratchet teeth for different sized syringes and/or material concentrations and hence variation of the quantity of material e.g. number of units delivered per ratchet tooth advance.

The various components of the dispensing device may be made of any conventional material depending on the functional requirements of the various components. Thus for example the spring 21 is conveniently made of spring steel whilst the body 3 and drive members 10, 14 are made of relatively rigid plastics materials, for example, polypropylene or polyacrylate. Advantageously the detachable front portion 4 is made of or incorporates a window of a a substantially transparent plastics material to permit observation of the forward end of the syringe 2 and enable quick and easy checking as to when the syringe is in, or is approaching, a fully discharged condition.

It will be appreciated by those skilled in the art that various modifications can be made to the above embodiment without departing from the scope of the present invention as defined in the following claims. Thus for example other forms of unidirectional drive transmission could be employed, for example, one or more balls or rollers disposed in a corresponding asymmetric generally wedge shaped recess or recesses formed in one of the drive members so that in the forward direction of movement of the first drive member a said ball or roller is jammed between one wedge surface and the other of said drive members to transmit drive therebetween and in the reverse direction the ball lies loosely between an opposite surface of the recess and said other drive member allowing the drive members to pass freely relative to each other.

A preferred form of ratchet means for the purposes of ease of manufacture etc. is illustrated in FIG. 3 of the drawings which shows a modified embodiment. In this embodiment the pawl 112 is formed integrally with the first drive member 11 being connected thereto by a thin web 29 and the first drive member being of a suitable material such that the web 29 is resiliently deformable and the pawl 112 is biased towards a position in engagement with the ratchet teeth 13 of the second drive member 14. The body member 3 is provided with lugs 30 on either side of the first drive member 11. At their forward ends the lugs are provided with cam surfaces 31 disposed for camming engagement by respective side portions of the pawl 112 which project laterally outwardly of the first drive member 11 on either side thereof. The lugs 30 are disposed so that as the first drive member 11 approaches its fully retracted position the pawl 112 comes into contact with the cam surfaces 31 of the lugs 30 and gradually rides up over them as retraction continues and is thereby displaced laterally from the ratchet teeth 13 until in the fully retracted position of the first drive member, the pawl 112 is fully clear of the ratchet teeth 13.

Thus in the fully retracted position of the first drive member 11 as shown in FIG. 3 the second drive member 14 is free to be retracted independently of the first drive member 11, in particular during insertion of a new syringe into the elongate body 3. As soon as the first drive member 11 is actuated and driven forward though, the pawl 112 returns into engagement with the ratchet teeth 13 and thus into unidirectional driving engagement with the second drive member 14.

Naturally still further modifications are also possible. Thus for example the lugs could be disposed in a position for camming engagement with an appropriate engagement surface on the pawl for displacement thereof to a fully disengaged position in a fully forward position of the first drive member so that new syringes can be inserted when the first drive member is held in a fully forward position. Also part or all of the barrel could be made of clear material to permit viewing of the full length of the syringe and thus permit monitoring of the discharge of the syringe from beginning to end.

What is claimed is:

1. A dispensing device suitable for use in dispensing a predetermined quantity of material from a container comprising a tubular body member having one end, said one end having an outlet, and a plunger slidably movable in said body member towards said outlet, said dispensing device comprising:
    an elongate body having a first end portion and defining a chamber for receiving a said container with said outlet of said container held in said first end portion of the elongate body;
    a first drive member slidably mounted on said body;
    an unidirectional drive transmission means disposed for driving engagement with said first drive member, at least in use of the device;
    a second drive member having a free end, said free end being drivingly engageable with said plunger of the container, in use of the device, so that said second drive member and said plunger can be driven by the first drive member via said unidirectional drive transmission means, in use of the device for dispensing, only in a direction towards the container outlet and the first end portion of the elongated body whilst permitting return movement of the first drive member;
    said unidirectional drive transmission means comprising a plurality of ratchet teeth on one of said first and second drive members and a pawl means on the other disposed for unidirectional driving engagement with said ratchet teeth;
    said device including a resilient biasing means disposed in said elongate body for biasing said first drive member in a direction for providing return movement of said first drive member;
    wherein one of said elongate body and first drive member is provided with a stop means and the other with axially spaced apart first and second abutment means, said abutment means being disposed on either side of said stop means for co-operation therewith so as to define a maximal displacement of the first drive member thereby to determine a maximal dispensing dose for a single stroke of the first drive member.

2. The device of claim 1 wherein is mounted in said chamber a said container with said plunger thereof disposed for driven engagement with said second drive member.

3. The device of claim 2 wherein said container is a hypodermic syringe.

4. The device of claim 3 wherein the second drive member is formed integrally with the plunger of said hypodermic syringe.

5. The device of claim 3 wherein said syringe contains a medicament.

6. The device of claim 1 wherein said elongate body is provided with a detachable front portion for retaining said container in said elongate body and permitting insertion and removal of said container from the elongate body when said front portion is detached.

7. The device of claim 6 wherein said unidirectional drive transmission is disengagable to permit retraction of the second drive member upon insertion of the container into the elongate body.

8. A dispensing device suitable for use in dispensing a predetermined quantity of material from a container comprising a tubular body member having one end, said one end having an outlet, and a plunger slidably movable in said body member towards said outlet, said dispensing device comprising:

an elongate body having a first end portion and defining a chamber for receiving a said container with said outlet of said container held in said first end portion of the elongate body;

a first drive member slidably mounted on said body;

an unidirectional drive transmission means disposed for driving engagement with said first drive member, at least in use of the device;

a second drive member having a free end, said free end being drivingly engageable with said plunger of the container, in use of the device, so that said second drive member and said plunger can be driven by the first drive member via said unidirectional drive transmission means, in use of the device for dispensing, only in a direction towards the container outlet and the first end portion of the elongate body whilst permitting return movement of the first drive member;

said unidirectional drive transmission means comprising a plurality of ratchet teeth on one of said first and second drive members and a pawl means on the other disposed for unidirectional driving engagement with said ratchet teeth;

said device including a resilient biasing means disposed in said elongate body for biasing said first drive member in a direction for providing return movement of said first drive member;

wherein one of said elongate body and first drive member is provided with axially spaced apart first and second abutment means and the other is provided with first and second stop means surfaces, said stop means surfaces being disposed for cooperation with respective ones of said first and second abutment means in respective end limit positions of the first drive member thereby to define a maximal displacement of the first drive member corresponding to a maximal dispensing dose for a single stroke of the first drive member.

* * * * *